(12) United States Patent
Azad et al.

(10) Patent No.: US 9,873,706 B2
(45) Date of Patent: Jan. 23, 2018

(54) PROCESS FOR THE PREPARATION OF BARICITINIB AND AN INTERMEDIATE THEREOF

(71) Applicant: SUN PHARMACEUTICAL INDUSTRIES LIMITED, Mumbai, Maharashtra (IN)

(72) Inventors: Md Abul Kalam Azad, Karimgang (IN); Gyanendra Pandey, Faridabad (IN); Kaptan Singh, Gurgaon (IN); Mohan Prasad, Gurgaon (IN)

(73) Assignee: Sun Pharmaceutical Industries Limited, Mumbai (IN)

( * ) Notice: Subject to any disclaimer, the term of this patent is extended or adjusted under 35 U.S.C. 154(b) by 0 days.

(21) Appl. No.: 15/532,573

(22) PCT Filed: Dec. 4, 2015

(86) PCT No.: PCT/IB2015/059364
§ 371 (c)(1),
(2) Date: Jun. 2, 2017

(87) PCT Pub. No.: WO2016/088094
PCT Pub. Date: Jun. 9, 2016

(65) Prior Publication Data
US 2017/0327507 A1 Nov. 16, 2017

(30) Foreign Application Priority Data
Dec. 5, 2014 (IN) .......................... 3554/DEL/2014

(51) Int. Cl.
*C07D 487/00* (2006.01)
*C07D 487/04* (2006.01)
*C07D 205/04* (2006.01)
*C07D 231/10* (2006.01)

(52) U.S. Cl.
CPC ......... *C07D 487/04* (2013.01); *C07D 205/04* (2013.01); *C07D 231/10* (2013.01)

(58) Field of Classification Search
CPC ................................................. C07D 487/04
USPC ............................................................ 544/280
See application file for complete search history.

(56) References Cited

U.S. PATENT DOCUMENTS

| 8,158,616 B2 | 4/2012 | Rodgers et al. |
| 2013/0225556 A1 | 8/2013 | Rodgers et al. |
| 2013/0253190 A1 | 9/2013 | Zhou |
| 2014/0228348 A1 | 8/2014 | Brubaker et al. |

FOREIGN PATENT DOCUMENTS

WO 2010/083283 A2 7/2010

OTHER PUBLICATIONS

International Search Report for PCT/IB2015/059364, dated Mar. 11, 2016.
Written Opinion of the International Searching Authority for PCT/IB2015/059364, dated Mar. 11, 2016.
International Preliminary Report on Patentability for PCT/IB2015/059364, dated Jun. 6, 2017.

*Primary Examiner* — Jeffrey H Murray
(74) *Attorney, Agent, or Firm* — Medler Ferro Woodhouse & Mills

(57) ABSTRACT

The present invention provides a process for the preparation of baricitinib and an intermediate thereof. The present invention provides a convenient, economical, and industrially advantageous two-step process for the preparation of [4-(1H-pyrazol-4-yl)-7Hpyrrolo[2,3-d] pyrimidin-7-yl] methyl pivalate of Formula (II). The process of the present invention involves the use of an alkali or alkaline earth metal hydroxide, carbonate, or bicarbonate as a base for reacting 4-chloro-7H-pyrrolo[2,3-d]pyrimidine of Formula (III) with chloromethyl pivalate of Formula (IV), and the use of an unprotected pyrazole borolane of Formula (VIII) for the conversion of (4-chloro-7H-pyrrolo[2,3-d] pyrimidin-7-yl) methyl 2,2-dimethylpropanoate of Formula V into [4-(1H-pyrazol-4-yl)-7Hpyrrolo[2,3-d]pyrimidin-7-yl]methyl pivalate of Formula (II). The process of the present invention provides [4-(1H-pyrazol-4-yl)-7H-pyrrolo[2,3-d]pyrimidin-7-yl]methyl pivalate of Formula (I) in high yield.

9 Claims, No Drawings

PROCESS FOR THE PREPARATION OF BARICITINIB AND AN INTERMEDIATE THEREOF

FIELD OF THE INVENTION

The present invention provides a process for the preparation of baricitinib and an intermediate thereof.

BACKGROUND OF THE INVENTION

Baricitinib is a Janus kinase (JAK) inhibitor. It is chemically designated as {1-(ethylsulfonyl)-3-[4-(7H-pyrrolo[2,3-d]pyrimidin-4-yl)-1H-pyrazol-1-yl]azetidin-3-yl}acetonitrile, having the structure as depicted in Formula I.

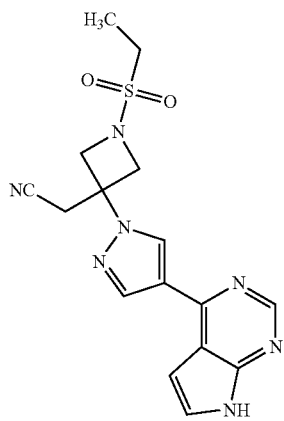

Formula I

U.S. Pat. No. 8,158,616 discloses processes for the preparation of baricitinib of Formula I and [4-(1H-pyrazol-4-yl)-7H-pyrrolo[2,3-d]pyrimidin-7-yl]methyl pivalate of Formula II.

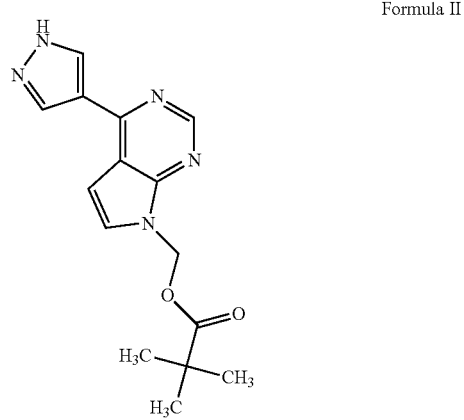 [SMILES: CC(C)(C)C(=O)OCn1ccc2c(-c3cn[nH]c3)ncnc21]

Formula II

U.S. Pat. No. 8,158,616 involves a three-step process for the preparation of [4-(1H-pyrazol-4-yl)-7H-pyrrolo [2,3-d] pyrimidin-7-yl]methyl pivalate of Formula II as depicted in Scheme 1 below:

Scheme 1

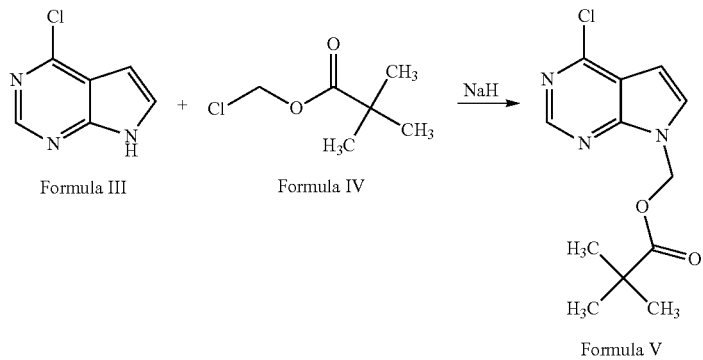

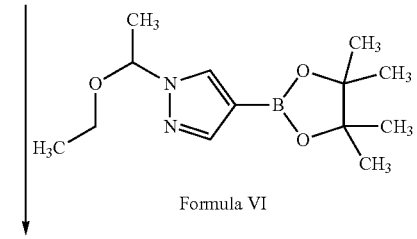

Formula VI

-continued

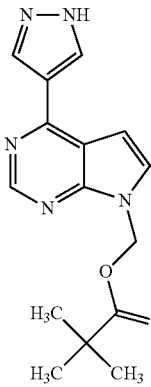

Formula II

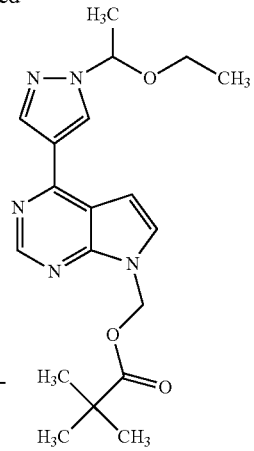

Formula VII

The process disclosed in U.S. Pat. No. 8,158,616 involves the use of sodium hydride as a base for reacting 4-chloro-7H-pyrrolo[2,3-d]pyrimidine of Formula III with chloromethyl pivalate of Formula IV, and the use of a protected pyrazole borolane derivative of Formula VI for the conversion of (4-chloro-7H-pyrrolo[2,3-d]pyrimidin-7-yl)methyl 2,2-dimethylpropanoate of Formula V into [4-(1H-pyrazol-4-yl)-7H-pyrrolo[2,3-d]pyrimidin-7-yl]methyl pivalate of Formula II.

The use of sodium hydride is not suitable on an industrial scale due to its inflammable and hazardous nature. The use of a protected pyrazole borolane derivative of Formula VI increases the cost of the manufacturing process, as an additional deprotection step is required for obtaining [4-(1H-pyrazol-4-yl)-7H-pyrrolo [2,3-d]pyrimidin-7-yl]methyl pivalate of Formula II.

Thus, there exists a need for the development of an economical and industrially advantageous process for the preparation of [4-(1H-pyrazol-4-yl)-7H-pyrrolo[2,3-d]pyrimidin-7-yl]methyl pivalate of Formula II that avoids the use of sodium hydride and involves a lesser number of steps.

SUMMARY OF THE INVENTION

The present invention provides a convenient, economical, and industrially advantageous two-step process for the preparation of [4-(1H-pyrazol-4-yl)-7H-pyrrolo[2,3-d]pyrimidin-7-yl]methyl pivalate of Formula II. The process of the present invention involves the use of an alkali or alkaline earth metal hydroxide, carbonate, or bicarbonate as a base for reacting 4-chloro-7H-pyrrolo[2,3-d]pyrimidine of Formula III with chloromethyl pivalate of Formula IV, and the use of an unprotected pyrazole borolane of Formula VIII for the conversion of (4-chloro-7H-pyrrolo[2,3-d]pyrimidin-7-yl)methyl 2,2-dimethylpropanoate of Formula V into [4-(1H-pyrazol-4-yl)-7H-pyrrolo[2,3-d]pyrimidin-7-yl]methyl pivalate of Formula II. The process of the present invention provides [4-(1H-pyrazol-4-yl)-7H-pyrrolo[2,3-d]pyrimidin-7-yl]methyl pivalate of Formula II in high yield.

A first aspect of the present invention provides a process for the preparation of [4-(1H-pyrazol-4-yl)-7H-pyrrolo [2,3-d]pyrimidin-7-yl]methyl pivalate of Formula II, Formula II

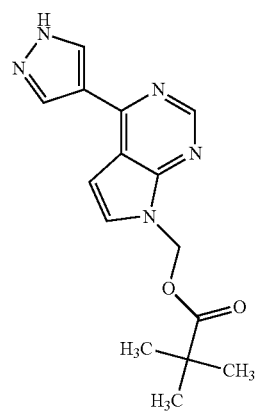

comprising the steps of:
i) reacting 4-chloro-7H-pyrrolo[2,3-d]pyrimidine of Formula III Formula III

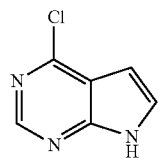

with chloromethyl pivalate of Formula IV

Formula IV

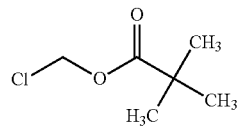

in the presence of an alkali or alkaline earth metal hydroxide, carbonate, or bicarbonate as a base to obtain (4-chloro-7H-pyrrolo[2,3-d]pyrimidin-7-yl)methyl 2,2-dimethylpropanoate of Formula V; and

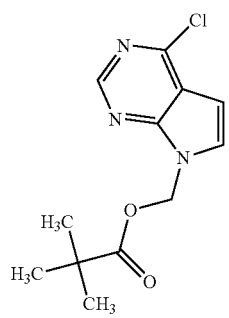

Formula V ii) reacting the (4-chloro-7H-pyrrolo[2,3-d]pyrimidin-7-yl)methyl 2,2-dimethylpropanoate of Formula V with 4-(4,4,5,5-tetramethyl-1,3,2-dioxaborolan-2-yl)-1H-pyrazole of Formula VIII

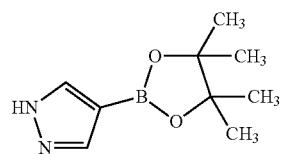

Formula VIII to obtain the [4-(1H-pyrazol-4-yl)-7H-pyrrolo[2,3-d]pyrimidin-7-yl]methyl pivalate of Formula II.

A second aspect of the present invention provides a process for the preparation of baricitinib of Formula I,

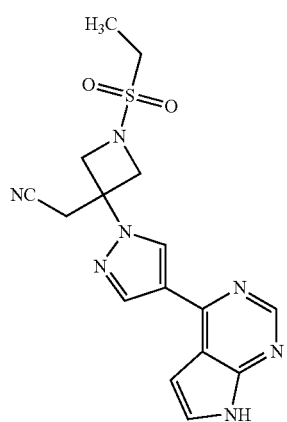

Formula I comprising the steps of:
i) reacting 4-chloro-7H-pyrrolo[2,3-d]pyrimidine of Formula III

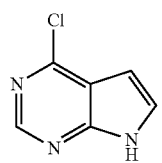

Formula III with chloromethyl pivalate of Formula IV

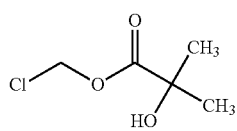

Formula IV in the presence of an alkali or alkaline earth metal hydroxide, carbonate, or bicarbonate base to obtain (4-chloro-7H-pyrrolo[2,3-d]pyrimidin-7-yl)methyl 2,2-dimethylpropanoate of Formula V;

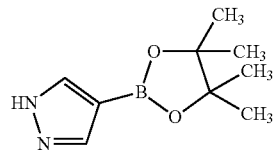

Formula V ii) reacting the (4-chloro-7H-pyrrolo[2,3-d]pyrimidin-7-yl)methyl 2,2-dimethylpropanoate of Formula V with 4-(4,4,5,5-tetramethyl-1,3,2-dioxaborolan-2-yl)-1H-pyrazole of Formula VIII

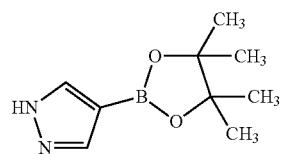

Formula VIII to obtain [4-(1H-pyrazol-4-yl)-7H-pyrrolo [2,3-d]pyrimidin-7-yl]methyl pivalate of Formula II; and

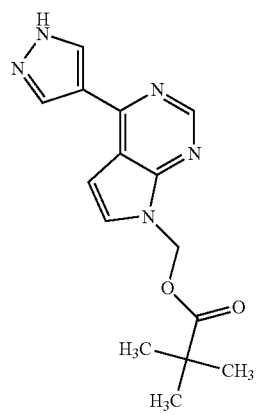

Formula II iii) reacting the [4-(1H-pyrazol-4-yl)-7H-pyrrolo [2,3-d]pyrimidin-7-yl]methyl pivalate of Formula II with [1-(ethylsulfonyl)azetidin-3-ylidene]acetonitrile of Formula IX

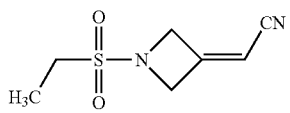

Formula IX to obtain baricitinib of Formula I.

DETAILED DESCRIPTION OF THE INVENTION

Various embodiments and variants of the present invention are described hereinafter.

The term "about," as used herein, refers to any value which lies within the range defined by a number up to ±10% of the value.

The term "ambient temperature," as used herein, refers to a temperature in the range of about 20° C. to about 35° C.

The reaction of 4-chloro-7H-pyrrolo[2,3-d]pyrimidine of Formula III with chloromethyl pivalate of Formula IV is carried out in the presence of an alkali or alkaline earth metal hydroxide, carbonate, or bicarbonate as a base. Examples of alkali and alkaline earth metal hydroxides include lithium hydroxide, sodium hydroxide, potassium hydroxide, magnesium hydroxide, calcium hydroxide, and barium hydroxide. Examples of alkali and alkaline earth metal carbonates include sodium carbonate, potassium carbonate, calcium carbonate, and magnesium carbonate. Examples of alkali metal bicarbonates include sodium bicarbonate and potassium bicarbonate. In an embodiment of the present invention, the reaction of 4-chloro-7H-pyrrolo[2,3-d]pyrimidine of Formula III with chloromethyl pivalate of Formula IV is carried out in the presence of potassium carbonate.

The reaction of 4-chloro-7H-pyrrolo[2,3-d]pyrimidine of Formula III with chloromethyl pivalate of Formula IV is carried out at ambient temperature in the presence of a solvent. Examples of solvents include hydrocarbons, ethers, chlorinated hydrocarbons, ketones, amides, sulphoxides, water, and mixtures thereof. Examples of hydrocarbons include benzene, toluene, and xylene. Examples of ethers include diethyl ether, ethyl methyl ether, di-isopropyl ether, tetrahydrofuran, and 1,4-dioxane. Examples of chlorinated hydrocarbons include dichloromethane and chloroform. Examples of ketones include acetone, dimethyl ketone, ethyl methyl ketone, and methyl iso-butyl ketone. Examples of amides include N,N-dimethylformamide and N,N-dimethylacetamide. Examples of sulphoxides include dimethyl sulphoxide and diethyl sulphoxide. In an embodiment of the present invention, the solvent used is N,N-dimethylformamide.

The reaction of 4-chloro-7H-pyrrolo[2,3-d]pyrimidine of Formula III with chloromethyl pivalate of Formula IV is carried out in about 4 hours to about 24 hours. In an embodiment of the present invention, the reaction is carried out in about 14 hours to about 18 hours.

The reaction of (4-chloro-7H-pyrrolo[2,3-d]pyrimidin-7-yl)methyl 2,2-dimethylpropanoate of Formula V with 4-(4,4,5,5-tetramethyl-1,3,2-dioxaborolan-2-yl)-1H-pyrazole of Formula VIII is carried out in the presence of a base in a solvent. The base may be selected from the group consisting of inorganic and organic bases. Examples of inorganic bases include alkali and alkaline earth metal hydroxides, carbonates, and bicarbonates. Examples of alkali and alkaline earth metal hydroxides include lithium hydroxide, sodium hydroxide, potassium hydroxide, magnesium hydroxide, calcium hydroxide, and barium hydroxide. Examples of alkali and alkaline earth metal carbonates include sodium carbonate, potassium carbonate, calcium carbonate, and magnesium carbonate. Examples of alkali metal bicarbonates include sodium bicarbonate and potassium bicarbonate. Examples of organic bases include N,N-diisopropylethylamine, triethylamine, triisopropylamine, N,N-2-trimethyl-2-propanamine, N-methylmorpholine, 4-dimethylaminopyridine, 2,6-di-tert-butyl-4-dimethylaminopyridine, 1,4-diazabicyclo[2.2.2]octane, and 1,8-diazabicyclo[5.4.0]undec-7-ene. In an embodiment of the present invention, potassium carbonate is used as the base. Examples of solvents include hydrocarbons, ethers, chlorinated hydrocarbons, ketones, amides, sulphoxides, water, and mixtures thereof. Examples of hydrocarbons include benzene, toluene, and xylene. Examples of ethers include diethyl ether, ethyl methyl ether, di-isopropyl ether, tetrahydrofuran, and 1,4-dioxane. Examples of chlorinated hydrocarbons include dichloromethane and chloroform. Examples of ketones include acetone, dimethyl ketone, ethyl methyl ketone, and methyl iso-butyl ketone. Examples of amides include N,N-dimethylformamide and N,N-dimethylacetamide. Examples of sulphoxides include dimethyl sulphoxide and diethyl sulphoxide. In an embodiment of the present invention, the reaction of (4-chloro-7H-pyrrolo[2,3-d]pyrimidin-7-yl)methyl 2,2-dimethylpropanoate of Formula V with 4-(4,4,5,5-tetramethyl-1,3,2-dioxaborolan-2-yl)-1H-pyrazole of Formula VIII is carried out in the presence of water and 1,4-dioxane.

The reaction of (4-chloro-7H-pyrrolo[2,3-d]pyrimidin-7-yl)methyl 2,2-dimethylpropanoate of Formula V with 4-(4,4,5,5-tetramethyl-1,3,2-dioxaborolan-2-yl)-1H-pyrazole of Formula VIII is initiated by adding a palladium catalyst. Examples of palladium catalysts include tetrakis(triphenylphosphine)palladium(0) and tetrakis(tri(o-tolyl)phosphine)palladium(0). In an embodiment of the present invention, the catalyst used is tetrakis(triphenylphosphine)palladium(0).

The reaction of (4-chloro-7H-pyrrolo[2,3-d]pyrimidin-7-yl)methyl 2,2-dimethylpropanoate of Formula V with 4-(4,4,5,5-tetramethyl-1,3,2-dioxaborolan-2-yl)-1H-pyrazole of Formula VIII is carried out at ambient temperature to the reflux temperature of the solvent. In an embodiment of the present invention, the reaction is carried out at a temperature of about 65° C. to about 90° C.

The reaction of (4-chloro-7H-pyrrolo[2,3-d]pyrimidin-7-yl)methyl 2,2-dimethylpropanoate of Formula V with 4-(4,4,5,5-tetramethyl-1,3,2-dioxaborolan-2-yl)-1H-pyrazole of Formula VIII is carried out in about 4 hours to about 24 hours. In an embodiment of the present invention, the reaction is carried out in about 14 hours to about 18 hours.

The isolation of [4-(1H-pyrazol-4-yl)-7H-pyrrolo[2,3-d]pyrimidin-7-yl]methyl pivalate of Formula II and (4-chloro-7H-pyrrolo[2,3-d]pyrimidin-7-yl)methyl 2,2-dimethylpropanoate of Formula V is carried out by concentration, precipitation, cooling, filtration, centrifugation, or a combination thereof, followed by drying. Drying is carried out under reduced pressure at a temperature of about 35° C. to about 60° C. for about 5 hours to about 24 hours.

The reaction of [4-(1H-pyrazol-4-yl)-7H-pyrrolo[2,3-d]pyrimidin-7-yl]methyl pivalate of Formula II with 2-(1-ethylsufonyl)azetidin-3-ylidene)acetonitrile of Formula IX to obtain baricitinib of Formula I may be carried out by the process disclosed in U.S. Pat. No. 8,158,616, which is incorporated herein by reference.

While the present invention has been described in terms of its specific aspects and embodiments, certain modifications and equivalents will be apparent to those skilled in the art, and are intended to be included within the scope of the present invention.

The following examples are for illustrative purposes only and should not be construed as limiting the scope of the invention in any way.

EXAMPLES

Example 1: Preparation of (4-chloro-7H-pyrrolo[2,3-d]pyrimidin-7-yl)methyl 2,2-dimethylpropanoate (Formula V)

4-Chloro-7H-pyrrolo[2,3-d]pyrimidine (25 g; Formula III), potassium carbonate (27 g), and chloromethyl pivalate (27 g; Formula IV) were added to a reaction vessel containing N,N-dimethylformamide (100 mL) at ambient temperature. The reaction mixture was stirred for 14 hours. The progress of the reaction was monitored by thin layer chromatography. Water (250 mL) was added to the reaction mixture, and then the mixture was stirred for 2 hours. The reaction mixture was filtered, then washed with water (50 mL), and then dried under reduced pressure at 40° C. to 45° C. for 12 hours to obtain (4-chloro-7H-pyrrolo[2,3-d]pyrimidin-7-yl)methyl 2,2-dimethylpropanoate.
Yield: 98.85%

Example 2: Preparation of [4-(1H-pyrazol-4-yl)-7H-pyrrolo[2,3-d]pyrimidin-7-yl]methyl pivalate (Formula II)

(4-Chloro-7H-pyrrolo[2,3-d]pyrimidin-7-yl)methyl 2,2-dimethylpropanoate (10 g; Formula V), water (50 mL), and potassium carbonate (15.5 g) were added into a reaction vessel at ambient temperature. 4-(4,4,5,5-Tetramethyl-1,3,2-dioxaborolan-2-yl)-1H-pyrazole (8.7 g; Formula VIII), 1,4-dioxane (100 mL), and tetrakis(triphenylphosphine)palladium(0) (0.08 g) were added to the reaction mixture. The reaction mixture was heated to a temperature of 80° C. to 85° C., and then stirred at the same temperature for 14 hours. The progress of the reaction was monitored by thin layer chromatography. On completion, ethyl acetate (100 mL) was added to the reaction mixture. The contents were stirred for 1 hour, then filtered through a Hyflo®, and then washed with ethyl acetate (40 mL). The organic layer was separated, and then concentrated under reduced pressure to obtain [4-(1H-pyrazol-4-yl)-7H-pyrrolo[2,3-d]pyrimidin-7-yl]methyl pivalate.
Yield: 82.27%

We claim:
1. A process for the preparation of [4-(1H-pyrazol-4-yl)-7H-pyrrolo[2,3-d]pyrimidin-7-yl]methyl pivalate of Formula II,

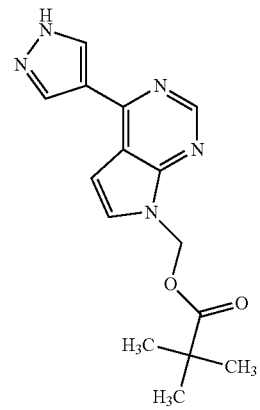

Formula II comprising the steps of:
i) reacting 4-chloro-7H-pyrrolo[2,3-d]pyrimidine of Formula III

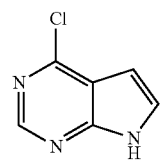

Formula III with chloromethyl pivalate of Formula IV

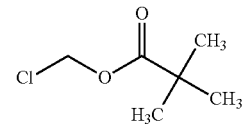

Formula IV in the presence of an alkali or alkaline earth metal hydroxide, carbonate, or bicarbonate base to obtain (4-chloro-7H-pyrrolo[2,3-d]pyrimidin-7-yl)methyl 2,2-dimethylpropanoate of Formula V; and

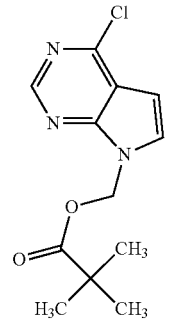

Formula V ii) reacting the (4-chloro-7H-pyrrolo[2,3-d]pyrimidin-7-yl)methyl 2,2-dimethylpropanoate of Formula V with 4-(4,4,5,5-tetramethyl-1,3,2-dioxaborolan-2-yl)-1H-pyrazole of Formula VIII Formula VIII

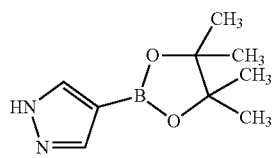

to obtain the [4-(1H-pyrazol-4-yl)-7H-pyrrolo[2,3-d]pyrimidin-7-yl]methyl pivalate of Formula II.

2. A process for the preparation of baricitinib of Formula I,

Formula I

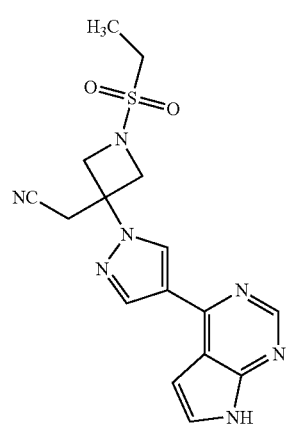

comprising the steps of:

i) reacting 4-chloro-7H-pyrrolo[2,3-d]pyrimidine of Formula III

Formula III

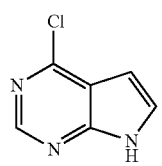

with chloromethyl pivalate of Formula IV

Formula IV

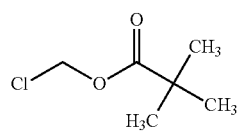

in the presence of an alkali or alkaline earth metal hydroxide, carbonate, or bicarbonate base to obtain (4-chloro-7H-pyrrolo[2,3-d]pyrimidin-7-yl)methyl 2,2-dimethylpropanoate of Formula V;

Formula V

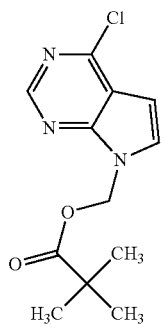

ii) reacting the (4-chloro-7H-pyrrolo[2,3-d]pyrimidin-7-yl)methyl 2,2-dimethylpropanoate of Formula V with 4-(4,4,5,5-tetramethyl-1,3,2-dioxaborolan-2-yl)-1H-pyrazole of Formula VIII Formula VIII

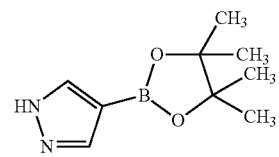

to obtain [4-(1H-pyrazol-4-yl)-7H-pyrrolo[2,3-d]pyrimidin-7-yl]methyl pivalate of Formula II; and Formula II

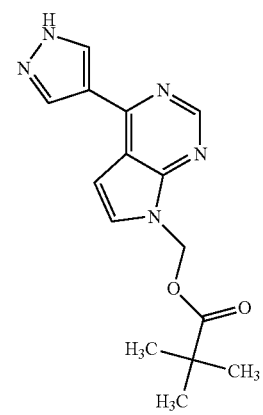

iii) reacting the [4-(1H-pyrazol-4-yl)-7H-pyrrolo[2,3-d]pyrimidin-7-yl]methyl pivalate of Formula II with [1-(ethylsulfonyl)azetidin-3-ylidene]acetonitrile of Formula IX Formula IX

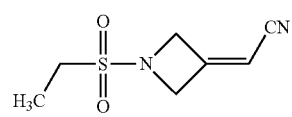

to obtain baricitinib of Formula I.

3. The process according to claim 1 or 2, wherein the alkali or alkaline earth metal hydroxide is selected from the group consisting of lithium hydroxide, sodium hydroxide, potassium hydroxide, magnesium hydroxide, calcium hydroxide, and barium hydroxide.

4. The process according to claim 1 or 2, wherein the alkali or alkaline earth metal carbonate is selected from the group consisting of sodium carbonate, potassium carbonate, calcium carbonate, and magnesium carbonate.

5. The process according to claim 1 or 2, wherein the alkali metal bicarbonate is selected from sodium bicarbonate and potassium bicarbonate.

6. The process according to claim 1 or 2, wherein the reaction of 4-chloro-7H-pyrrolo[2,3-d]pyrimidine of Formula III with chloromethyl pivalate of Formula IV is carried out at ambient temperature.

7. The process according to claim 1 or 2, wherein the reaction of 4-chloro-7H-pyrrolo[2,3-d]pyrimidine of Formula III with chloromethyl pivalate of Formula IV is carried out in the presence of a solvent.

8. The process according to claim 1 or 2, wherein the reaction of (4-chloro-7H-pyrrolo[2,3-d]pyrimidin-7-yl) methyl 2,2-dimethylpropanoate of Formula V with 4-(4,4,5,5-tetramethyl-1,3,2-dioxaborolan-2-yl)-1H-pyrazole of Formula VIII is carried out in the presence of an organic or inorganic base.

9. The process according to claim 7, wherein the solvent is selected from the group consisting of hydrocarbons, ethers, chlorinated hydrocarbons, ketones, amides, sulphoxides, water, and mixtures thereof.

* * * * *